United States Patent [19]
Freeland et al.

[11] Patent Number: 5,032,120
[45] Date of Patent: Jul. 16, 1991

[54] DISPOSABLE ABSORBENT ARTICLE HAVING IMPROVED LEG CUFFS

[75] Inventors: Mary E. Freeland, Norwood; Patrick J. Allen, Cincinnati, both of Ohio

[73] Assignee: The Procter & Gamble Company, Cincinnati, Ohio

[21] Appl. No.: 321,814
[22] Filed: Mar. 9, 1989
[51] Int. Cl.$^5$ .............................................. A61F 13/15
[52] U.S. Cl. ................................ 604/385.2; 604/385.1
[58] Field of Search ............................ 604/385.1, 385.2

[56] References Cited

U.S. PATENT DOCUMENTS

| | | | |
|---|---|---|---|
| 3,316,136 | 4/1967 | Pufahl | 156/160 |
| 3,860,003 | 1/1975 | Buell | 128/287 |
| 3,948,702 | 4/1976 | Theissen | 156/278 |
| 3,949,128 | 4/1976 | Ostermeier | 428/152 |
| 4,051,853 | 10/1977 | Egan | 604/390 |
| 4,209,563 | 6/1980 | Sisson | 428/288 |
| 4,210,144 | 7/1980 | Sarge et al. | 604/365 |
| 4,296,163 | 10/1981 | Emi et al. | 428/212 |
| 4,333,782 | 6/1982 | Pieniak | 156/164 |
| 4,397,645 | 8/1983 | Buell | 604/380 |
| 4,418,123 | 12/1983 | Bunnelle et al. | 428/517 |
| 4,450,026 | 5/1984 | Pieniak et al. | 156/164 |
| 4,525,407 | 6/1985 | Ness | 428/138 |
| 4,543,099 | 9/1985 | Bunnelle et al. | 604/385 |
| 4,556,596 | 12/1985 | Meuli | 428/152 |
| 4,681,579 | 7/1987 | Toussant et al. | 604/385.1 |
| 4,695,278 | 9/1987 | Lawson | 604/385.2 |
| 4,704,116 | 11/1987 | Enloe | 604/385.2 |
| 4,738,677 | 4/1988 | Foreman | 604/385.2 |
| 4,743,246 | 5/1988 | Lawson | 604/385.2 |
| 4,789,699 | 12/1988 | Kieffer et al. | 524/271 |
| 4,795,454 | 1/1989 | Dragoo | 604/385.2 |
| 4,808,178 | 2/1989 | Aziz et al. | 604/385.2 |
| 4,813,946 | 3/1989 | Sabee | 604/385.2 |
| 4,816,025 | 3/1989 | Foreman | 604/385.2 |
| 4,938,757 | 7/1990 | Van Gompel et al. | 604/385.2 X |

FOREIGN PATENT DOCUMENTS 0059183  2/1975  Australia .......................... 604/385.1

Primary Examiner—Randall L. Green
Assistant Examiner—David H. Willse
Attorney, Agent, or Firm—Larry L. Huston; Steven W. Miller; Richard C. Witte

[57] ABSTRACT

A disposable absorbent article, such as a diaper, is disclosed. The diaper has two lengthwise extending longitudinal marginal portions, each longitudinal marginal portion having two elastically extensible leg cuffs, a barrier cuff and a gasket cuff. The leg cuffs serve to help contain body exudates within the disposable article. Each leg cuff is elasticized to provide a relatively low ultimate contact force against the skin of the wearer at relatively high elongations. This arrangement provides a diaper with leg cuffs which can be elongated to conform to the shape of the wearer, without causing undue discomfort or irritation to the legs of the wearer. The relatively low ultimate contact force at relatively high elongations may be accomplished either through a low contact force differential material, or through a material which exhibits stress relaxation over a relatively short period of time.

12 Claims, 2 Drawing Sheets

DISPOSABLE ABSORBENT ARTICLE HAVING IMPROVED LEG CUFFS

FIELD OF THE INVENTION

The present invention relates to disposable absorbent articles, such as diapers, and more particularly to disposable absorbent articles having leg cuffs which retain body exudates within the disposable article.

BACKGROUND OF THE INVENTION

Disposable absorbent articles, such as diapers, frequently utilize one or both of two types of leg cuffs, gasket leg cuffs and barrier leg cuffs. Gasket leg cuffs are used to seal the leg openings of the article about the wearer and to help prevent the leakage of body exudates from the article at the leg openings. For example, U.S. Pat. No. 3,860,003 issued Jan. 14, 1975 to Buell teaches a diaper having an elastically contractable side portion. U.S. Pat. No. 4,333,782 issued June 8, 1982 to Pieniak and U.S. Pat. No. 4,450,026 issued May 22, 1984 to Pieniak et al. teach diapers having an elastic film ribbon incorporated into the marginal edges of the diapers.

Barrier leg cuffs are utilized to provide improved containment of body exudates within the disposable absorbent article. For example, U.S. Pat. No. 4,704,115 issued Nov. 3, 1987 to Buell teaches a disposable garment having side edge leakage guard gutters which obviate inversion and unfolding during use by not encircling the thighs of the wearer. U.S. Pat. No. 4,808,178 issued Feb. 28, 1989, to Aziz et al. teaches a disposable article having leakage resistant flaps which are nonabsorbent and liquid-impermeable.

Other variations of barrier cuffs have been proposed, such as U.S. Pat. No. 4,795,452 issued Jan. 3, 1989 to Blaney et al. This reference teaches a disposable article having a cuff member with a cantilevered flap which provides a liquid-impermeable seal, a barrier wall which retards the flow of exudates and gasketing action about the legs of the wearer. U.S. Pat. No. 4,795,454 issued Jan. 3, 1989 to Dragoo teaches a disposable absorbent article having a barrier cuff with a distal edge and a proximal edge, with spacing means disposed at the distal edge and a seal formed at the proximal edge.

While many of the leg cuffs of the prior art are elasticized and elastically contractible, the prior art does not address how such elastication affects the comfort of the wearer, particularly with regard to red marking and the associated epidermal irritation, or how such leg cuffs may be utilized to advantageously shape the diaper. Therefore, it is an object of this invention to provide a diaper having leg cuffs which are leakage resistant and yet optimize wearer comfort. In accordance with one aspect of the present invention, a diaper having leg cuffs is provided, which leg cuffs have an ultimate contact force of less than about 270 grams per centimeter (1.5 pounds per inch) of width when elongated about 50 to about 350 per cent, and which have an incremental differential force of less than about 14 grams per centimeter of cumulative width of the elastic members.

SUMMARY OF THE INVENTION

The invention comprises a disposable absorbent article having a liquid impervious backsheet and a liquid pervious topsheet which is at least partially peripherally joined to the backsheet. An absorbent core is disposed intermediate the topsheet and the backsheet. The disposable article also has two transverse waist portions and two lengthwise extending longitudinal marginal portions, with each longitudinal marginal portion having at least one leg cuff. The leg cuff may be a barrier cuff or a gasket cuff, or the longitudinal marginal portion may have both a gasket cuff and a barrier cuff. Each leg cuff has at least one elastic member defining a cumulative width. The leg cuff and elastic member are elastically extensible in at least one direction. When extended, in tension, with a tensile force of about 270 grams per centimeter (1.5 pounds per inch) of cumulative width of the elastic members, the elastic member is elongated between about 50 and about 350 percent. Further, when the leg cuff is elongated in increments of about 50 percent, the incremental force is less than about 14 grams per centimeter of cumulative width of the elastic members. The elastic member may exhibit an elongation of about 50 to about 350 percent when extended with a tensile force about 270 grams per centimeter of width after about 10 minutes at a temperature of at least about 22° C.

BRIEF DESCRIPTION OF THE DRAWINGS

While the Specification concludes with claims particularly pointing out and distinctly claiming the invention, it is believed the invention will be better understood from the following drawings taken in conjunction with the Specification. In the drawings like parts are designated with the same reference numeral

DETAILED DESCRIPTION OF THE INVENTION

Figure 1:
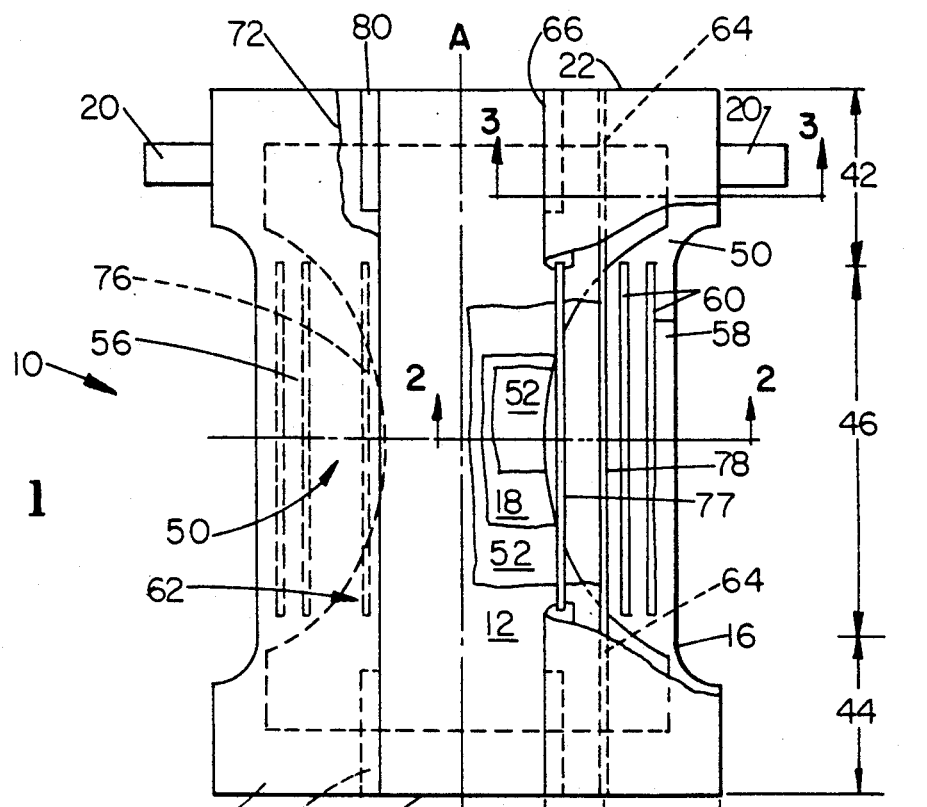
FIG. 1 is a top plan view of a diaper embodiment of the present invention, having no elastic induced contraction and showing the topsheet, tissue layers and core partially in cutaway.

Referring to FIG. 1, there is shown a disposable absorbent article 10, intended to be worn about the lower torso. As used herein, the term "disposable absorbent article" refers to a garment which collects or contains body exudates and is intended to be discarded after a single use and not to be laundered or restored. A "disposable diaper" is a particular disposable article worn by infants or incontinent persons and which is drawn between the legs, and fastened about the waist of the wearer.

A preferred diaper 10 comprises a liquid pervious topsheet 12, a liquid impervious backsheet 16, and an absorbent core 18 disposed intermediate the topsheet 12 and the backsheet 16. The topsheet 12 and the backsheet 16 are at least partially peripherally joined to ensure the core 18 is held in the desired position.

The topsheet 12 and the backsheet 16 generally define the periphery of the diaper 10. The periphery is the outer perimeter and greatest extent of the diaper 10. The periphery comprises a first end 22, a second end 24, and longitudinal marginal portions 50.

The diaper 10 has a transverse first waist portion 42 and a transverse second waist portion 44 extending respectively from the first end 22 and second end 24 of the diaper periphery towards the lateral center of the diaper 10 a distance of about one-fifth to about one-third the longitudinal length of the diaper 10. As used herein, the longitudinal dimension of the diaper 10 is that dimension which is aligned front to back with respect to the wearer as the diaper 10 is worn, and which parallels the longitudinal axis A—A. The transverse dimension of the article is generally orthogonal the longitudinal axis A—A and sideways aligned as the diaper 10 is worn by a wearer in the standing position. The waist portions 42 and 44 comprise those portions of the diaper 10 which, when worn, encircle the waist of the wearer and are generally at the highest elevation of the diaper 10 when the wearer is in the standing position. The crotch 46 of the diaper 10 is that portion of the diaper which is disposed between the first and second waist portions 42 and 44 and which, when worn, is positioned between the legs of the wearer.

The disposable diaper 10 may further comprise a fastening means 20 and a receiving surface (not shown). The fastening means 20 and the receiving surface maintain the waist portions 42 and 44 of the diaper 10 in an overlapping configuration while the diaper 10 is worn. This arrangement fits the diaper 10 to the wearer and forms a side closure. The elements of the diaper 10 may be assembled in a variety of configurations well known to one skilled in the art, with a preferred configuration being generally described in U.S. Pat. No. 3,860,003 issued Jan. 14, 1975 to Buell, which patent is incorporated herein by reference for the purpose of disclosing a well known and preferred diaper 10 configuration.

The diaper 10 further comprises at least one leg cuff 56 and 62 disposed in each longitudinal marginal portion 50. As used herein the phrase "leg cuff" is inclusive of both barrier cuffs 62, gasket cuffs 56 and combinations and variations thereof. As used herein the phrase "gasket cuff" is any portion of the diaper 10 generally coplanar of the topsheet 12 provided with a means to seal such portion about the leg of the wearer and the phrase "barrier cuff" is a particular leg cuff which has a means to space such leg cuff away from the topsheet 12.

The gasket cuffs 56 and the barrier cuffs 62 are preferably generally aligned in the longitudinal direction. A preferred diaper 10 construction has two gasket cuffs 56 and two barrier cuffs 62, disposed generally inboard of the gasket cuffs 56.

Each gasket cuff 56 comprises a gasketing flap 58 and one or more elastic members 60. Each barrier cuff 62 comprises a flap portion 68 and a channel portion 70. The channel portion 70 comprises a proximal edge 64, a distal edge 66, ends 72 and a spacing means 76, for spacing the distal edge 66 of the flap portion 68 from the topsheet 12. The proximal edge 64 of the channel portion 70 is joined preferably by an adhesive bead to a gasketing flaps 58. The ends 72 of each barrier cuff 62 are secured to an intermediate portion of the barrier cuff 62 by closing means 80.

Referring to FIG. 1, and examining the components of the diaper 10 in more detail, the topsheet 12 and backsheet 16 of the diaper 10 are generally coextensive and at least partially peripherally joined together as noted above. As used herein, the term "join" refers to the condition where a first member or component is affixed or connected to a second member or component, either directly or indirectly, where the first member or component is affixed or connected to an intermediate member or component which, in turn, is affixed or connected to the second member or component. The association between the first member or component and the second member or component is intended to remain for the life of the article. Joining of the topsheet 12 and the backsheet 16 may be accomplished by a hot-melt adhesive such as Eastobond A3 manufactured by the Eastman Chemical Products of Kingsport, Tenn.

The absorbent core 18 has length and width dimensions generally less than that of the topsheet 12 and the backsheet 16. The absorbent core 18 is interposed between the topsheet 12 and the backsheet 16, preferably in a fixed relationship.

The absorbent "core" may be any means for absorbing and retaining liquid body exudates. The absorbent core 18 is generally compressible, conformable, and nonirritating to the skin of the wearer. A preferred core 18 has first and second opposed faces and may, if desired, be further encased by one or more tissue layers 52. One opposed face of the core is oriented towards the topsheet 12 and the other opposed face of the core 18 is oriented towards the backsheet 16. The tissue layers 52 improve the tensile strength of the core 18 assembly and reduce the tendency of the absorbent core to split or clump when wetted. The tissue layers 52 may also help improve lateral wicking of the liquids and thereby more evenly distribute absorbed liquids throughout the absorbent core 18. A tissue layer 52 having a basis weight of approximately 16 grams per square meter (10 pounds per 3,000 square feet) and an air permeability of approximately 30 cubic meters per minute per square meter (100 cubic feet per minute per square foot) at a differential pressure of 13 millimeters (0.5 inch) of water works well.

The absorbent core 18 may assume a wide variety of sizes and shapes, such as rectangular or, as shown, be hourglass shaped. The absorbent core 18 may be made from a variety of commonly used materials such as comminuted wood pulp, typically referred to as airfelt. If desired, the absorbent core 18 may further contain absorbent gelling materials as is commonly used in the art.

The absorbent core 18 is superimposed on the backsheet 16 and preferably joined thereto by any means well known in the art, such as adhesive bonding. In a particularly preferred embodiment, adhesive bonding is accomplished by longitudinally oriented adhesive bands which join the core 18 to the backsheet 16.

The backsheet 16 is impervious to liquids, such as urine, and prevents liquids absorbed by and contained in the absorbent core 18 from wetting undergarments, clothing, bedding and other objects which contact the diaper 10. As used herein, the term "backsheet" refers to any barrier disposed outwardly of the core 18 as the diaper is worn and which contains absorbed liquids within the diaper 10. Preferably, the backsheet 16 is a polyolefinic film of about 0.01 to about 0.051 millimeters (0.0005–0.002 inches) in thickness. A polyethylene film is particularly preferred, with a suitable film being manufactured by the Clopay Company of Cincinnati, Ohio and marketed as Film P18-850. If desired, the backsheet 16 may be embossed or matte finished to provide a clothlike appearance or be provided with passages to permit escape of vapors.

The topsheet 12 is preferably compliant, tactilely pleasant and nonirritating to the skin of the wearer. The topsheet 12 prevents contact of the absorbent core 18 and liquids therein with the skin of the wearer. The topsheet 12 is liquid pervious, permitting liquids, particularly urine, to readily penetrate therethrough. As used herein, the term "topsheet" refers to any liquid pervious facing which contacts the skin of the wearer while the diaper 10 is worn and prevents substantial contact of the core 18 with the skin of the wearer.

A preferred topsheet 12 is carded and thermally bonded by means known to those skilled in the nonwoven fabrics art. A particularly preferred topsheet 12 has a weight of about 18 to about 25 grams per square meter, a minimum dry tensile strength of about 400 grams per centimeter in the machine direction and a wet tensile strength of at least about 55 grams per centimeter in the cross-machine direction.

Referring back to FIG. 1, the topsheet 12 may be peripherally joined to the backsheet 16 in any suitable manner as is well known in the art. The topsheet 12 is preferably continuously peripherally joined to the backsheet 16, although any embodiment in which the topsheet 12 is at least partially peripherally joined to the backsheet 16 sufficient to prevent disruption of the arrangement described herein is adequate. In a preferred embodiment, a multiplicity of longitudinal adhesive bands, preferably of hot melt adhesive, are applied to the backsheet 16 and the topsheet 12 is thereby peripherally joined to the backsheet 16.

As noted above, preferably the diaper 10 is provided with a fastening system 20 and a complementary receiving surface (not shown) for maintaining the first waist portion 42 and the second waist portion 44 in an overlapping configuration while the diaper 10 is worn. This arrangement secures the diaper 10 to the wearer. The fastening system 20 and the receiving surface should interact to resist the separation forces which occur while the diaper 10 is worn. The phrase "separation forces" refers to forces acting on the fastening system 20 and the receiving surface which tend to cause separation, release or removal of the fastening system 20 from the receiving surface. Separation forces include both shear and peel forces. The term "shear force" refers to distributive forces acting generally tangential to the plane of the fastening system 20 and the receiving surface and which may be thought of as being generally parallel to the plane of the fastening system 20. The term "peel force" refers to distributive forces acting in the direction away from the wearer as the diaper 10 is worn and may be thought of as having a component perpendicular to the plane of the fastening system 20 and the receiving surface.

Separation forces are typically generated by movements of the wearer or by the wearer trying to unfasten the diaper 10. Generally, an infant should not be able to unfasten or remove a diaper 10 that the infant is wearing, nor should the diaper 10 become unfastened in the presence of ordinary separation forces which occur during normal wearing periods. However, an adult should be able to remove the diaper 10 to change it when soiled or inspect the diaper 10 to see if soiling has occurred. Generally, the fastening system 20 and the receiving surface should preferably resist a peel force of at least about 200 grams, more preferably at least about 500 grams and even more preferably at least about 700 grams. The fastening system 20 and the receiving surface should preferably resist a shear force of at least about 500 grams, more preferably at least about 750 grams, and even more preferably at least about 1,000 grams.

The receiving surface may be disposed in a first position anywhere on the diaper 10, as long as the receiving surface engages the fastening system 20 to maintain the first and second waist portions 42 and 44 in an overlapping configuration. For example, the receiving surface may be disposed on the outside surface of the second waist portion 44, on the inside surface of the first waist portion 42, or any other position on the diaper 10 on which the receiving surface is disposed so as to engage the fastening system 20. The receiving surface may be integral, a discrete element joined to the diaper 10, or a portion of the diaper 10, such as the topsheet 12 or the backsheet 16.

Suitable fastening systems 20 include adhesive tapes and refastenable mechanical fastening systems. If an adhesive tape fastening system 20 is selected, a preferred construction has a generally Y-shaped cross-section and is shown in U.S. Pat. No. 3,848,594 issued Nov. 19, 1974 to Buell, which patent is incorporated herein by reference for the purpose of showing a suitable adhesive tape fastening system 20. If a refastenable mechanical fastening system 20 is selected, a preferred construction is shown in U.S. Pat. Application Ser. No. 07/132,281, Issue Batch No. N87 filed Nov. 18, 1987 in the name of Scripps, which application is incorporated herein by reference for the purpose of describing a particularly preferred refastenable mechanical fastening system 20.

Figure 2:
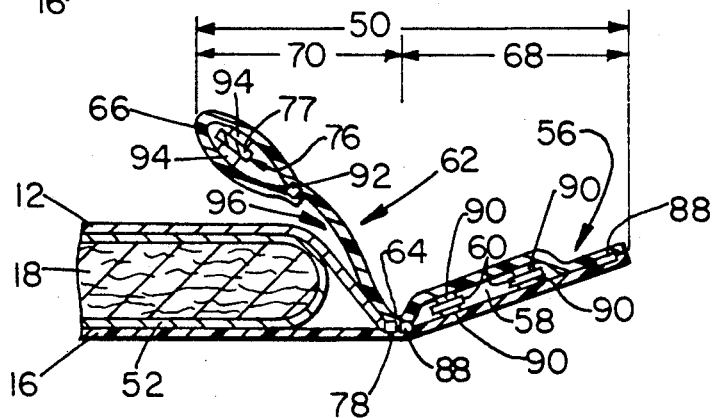
FIG. 2 is a fragmentary vertical sectional view of the diaper of FIG. 1, taken along line 2—2 of FIG. 1.

Referring to FIG. 2, the gasket cuffs 56 are elastically contractible and disposed near or adjacent the periphery of the diaper 10 in the longitudinal marginal portions 50 of the diaper 10. Preferably each gasket cuff 56 is disposed adjacent the barrier cuff 62 so that the gasket cuff 56 tends to draw and hold the diaper 10 against the legs of the wearer. Furthermore, a gasket cuff 56 may be transversely disposed in either or both of waist portions 42 or 44 of the diaper 10 to provide a waist cuff (not shown).

The gasket cuff 56 may comprise any of the several means well known in the art for sealing about the leg of the wearer. A particularly preferred gasket cuff 56 construction comprises a flexible gasketing flap 58 and one or more flap elastic members 60 as described in detail in U.S. Pat. No. 3,860,003 issued Jan. 20, 1975 to Buell and incorporated herein by reference for the purpose of showing a particularly preferred diaper gasket cuff 56 construction. Further, a method and apparatus suitable for manufacturing a disposable diaper 10 having elastically contractible gasket cuffs 56 are described in U.S. Pat. No. 4,081,30, issued Mar. 28, 1978, to Buell and incorporated herein by reference for the purpose of showing how such a diaper 10 and gasket cuffs 56 may be manufactured.

The gasketing flap 58 should be flexible and contractible so that the flap elastic members 60 may gather the gasketing flap 58 to provide a gasket cuff 56 about the legs or waist of the wearer. The gasketing flaps 58 are the portion of the diaper 10, particularly the longitudinal marginal portion 50, disposed between the periphery of the diaper 10 and the edges of the absorbent core 18. The flap portion 68 of the barrier cuff 62 and the backsheet 16 define the gasketing flap 58 and enclose the flap elastic member 60. In the preferred embodiment, the gasketing flaps 58 are formed from the extension of the backsheet 16 and the extension of the channel portion 70 of the barrier leg cuffs 62 which extends outwardly from and along the longitudinal side edges of the absorbent core 18 in the crotch region 46 of the diaper 10.

The flap elastic members 60 are operatively associated with the gasketing flaps 58 in an elastically contractible condition so that in a normally unrestrained configuration flap elastic members 60 effectively gather or contract the gasketing flaps 58. The flap elastic members 60 can be associated with the gasketing flaps in at least one of two ways. For example, the flap elastic members 60 may be stretched and secured to the gasketing flaps 58 while the gasketing flaps 58 are uncontracted. Alternatively, the gasketing flaps 58 may be contracted, for example by pleating, and the flap elastic members 60 joined to the contracted gasketing flaps 58 while the flap elastic members are in an unstretched state. As used herein, the phrase "operatively associated with" refers to the condition where two or more components act together.

In the embodiment of FIG. 1, the flap elastic members 60 extend essentially the entire longitudinal length of the gasket flaps 56 in the crotch region 46 of the diaper 10. Alternatively, the flap elastic members 60 may extend the entire longitudinal length of the diaper 10 or any other length, as desired, to provide an elastically contractible gasket cuff 56. The length of the flap elastic member 60 is dictated by the specific structure of the diaper 10. The gasket cuff 56 is preferably not disposed in the waist regions 42 and 44, so that the flap elastic members 60 do not extend into these portions of the gasketing flap 58 and are, therefore, not shown in FIG. 3.

The flap elastic members 60 are operatively associated with the gasketing flaps 58 by joining the flap elastic members 60 to the gasketing flaps 58 utilizing the pressure sensitive adhesive properties of the flap elastic members 60. In this arrangement (not shown), the flap elastic members 60 are directly joined to the gasketing flaps 58.

Figure 4:
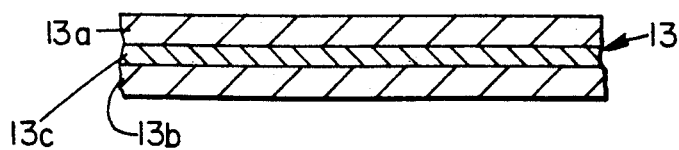
FIG. 4 is a fragmentary vertical sectional view of one embodiment of the elastic members of the leg cuffs of the present invention.

Alternatively, as shown by FIG. 2, the flap elastic members 60 may be operatively associated with the gasketing flap 58 by flap elastic attachment 90. This arrangement is particularly useful if a laminate 13, as shown in FIG. 4 is utilized for the flap elastic member 60. The flap elastic attachment 90 is preferably flexible and of sufficient adhesion to join the flap elastic member 60 in a stretched state. The flap elastic attachment 90 described herein is preferably glue beads made of hot melt adhesive, with an adhesive marketed by Findley Adhesives Incorporated of Elm Grove, Wis., under the tradename 581 having been found to work well. Alternatively, the flap elastic members 60 may be ultrasonically bonded or heat/pressure sealed to the diaper 10 using a variety of bonding patterns.

The flap elastic members 60 are secured in the gasket cuff 56 and the backsheet 16 by flap elastic attachment 90. The elastically contractible gasket cuff 56 is thereby formed by the gasketing flap 58 and the flap elastic member 60. A detailed description of the manner in which flap elastic members 60 may be disposed and joined to the diaper 10 is found in U.S. Pat. No. 4,25,461 issued Mar. 3, 1981, to Strickland et al., which patent is incorporated herein by reference for the purpose of showing alternative manners to join the flap elastic members 60 to the diaper 10.

With continuing reference to FIG. 2, it can be seen that the barrier leg cuffs 62 provide a barrier to restrain the free flow of body exudates along the topsheet 12 and provide a structure to hold and contain such exudates within the diaper 10. Each barrier cuff 62 is flexible, preferably having a channel portion 70, a flap portion 68 and a spacing means 76. As used herein, the term "flexible" refers to materials which are compliant and will readily conform to the general shape and contours of the wearer's body. The channel portion 70 is intermediate of and defined by a proximal edge 64 and a distal edge 66. The flap portion 68 is the portion of the barrier cuff 62 disposed outboard of the proximal edge 64 of the channel portion 70. The spacing means disposes the barrier cuff 62 away from the topsheet 12 towards the buttocks of the wearer.

The barrier cuffs 62 may be manufactured from a variety of materials such as polypropylene, polyester, rayon, nylon, foams, plastic films, formed films, and elastic foams. A number of manufacturing techniques may be used to manufacture the barrier cuffs 62. For example, the barrier cuffs 62 may be woven, nonwoven, spun-bonded, or carded. A particularly preferred barrier cuff 62 is liquid impermeable polypropylene containing no finish or surfactant. A particularly preferred polypropylene material is manufactured by James River Corporation of Richmond, Virginia under the tradename Celestra.

The barrier cuffs 62 are preferably hydrophobic and more preferably liquid impermeable so as to prevent the strikethrough of body exudates. A liquid impermeable barrier cuff 62 retards the movement of liquid through the barrier cuff 62, thereby making it more leakage resistant. The barrier cuffs 62 may be rendered liquid impermeable in any manner well known in the art such as selectively treating the barrier cuffs, untreating the barrier cuffs, or by securing a separate material to the barrier cuffs.

The flap portion 68 of the barrier cuff 62 is contiguous the channel portion 70 and extends outwardly from the proximal edge 64 of the channel portion 70 - towards the longitudinal edge of the diaper 10, and preferably to the longitudinal edge. The flap portion 68 of the barrier cuff 62 is formed by joining portions of a separate barrier cuff member to the backsheet 16, adjacent the longitudinal marginal portion 50 of the diaper 10. Joining is preferably accomplished with an adhesive or other attachment means 88, forming a leakage resistant seal at the attachment means 88, the extension of the flap portion 68 and the backsheet 16 to provide protection against leakage of liquids wicking along the topsheet 12.

Figure 3:
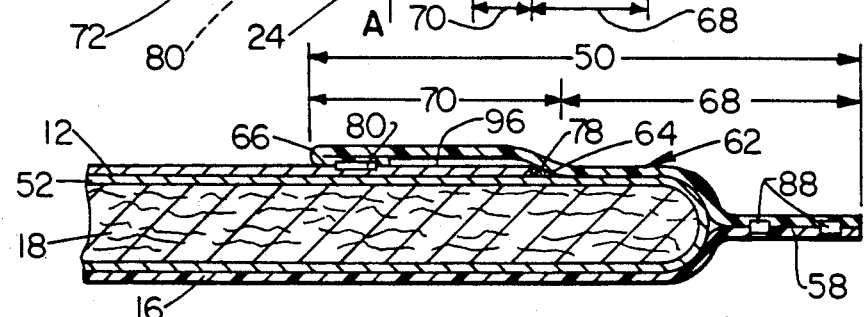
FIG. 3 is a fragmentary vertical sectional view of the diaper of FIG. 1, taken along line 3—3 of FIG. 1.

The topsheet 12 is positioned adjacent the body facing surface of the absorbent core 18 and extends beyond the side edge of the absorbent core 18, terminating inwardly of and preferably adjacent the proximal edge 64 of the channel portion 70 of the barrier cuff 62, where the topsheet 12 is preferably joined to the gasketing flap 58 and the proximal edge 64 by the seal means 78, to provide a leakage resistant seal at and along the proximal edge 64. As shown in FIG. 3, the flap portion 68 of the barrier cuff 62 is formed by joining portions of a separate barrier cuff member to the backsheet 16 adjacent the longitudinal marginal portion 50 of the diaper 10 with attachment means 88. Preferably attachment means 88 is an adhesive, forming a leakage resistant seal between the attachment means 88, the flap portion 68, and the backsheet 16 to provide protection against leakage of liquids emanating from the edges of the absorbent core 18 or wicking past the seal along the proximal edge 64 of the channel portion 70 of the barrier cuff 62. The flap portion 68 of the barrier cuff 62 and the backsheet 16 define the gasketing flap 58.

While the flap portion 68 is preferably a continuous segment of the barrier cuff member, the flap portion 68 may be formed from a different piece of material secured to the channel portion 70 of the barrier cuff 62. Thus, the flap portion 68 may have different physical properties, dimensions, and characteristics than the channel portion 70. For example, the flap portion 68 need not be liquid impermeable nor extend outwardly to the longitudinal edge of the diaper 10. In addition, each of the barrier cuffs 62 need not have a flap portion 68 such that the flap portion 68 may be omitted entirely. The flap portion 68 is, however, preferably hydrophobic, liquid impermeable, compliant, tactilely pleasant and nonirritating to the skin of the wearer because the flap portion 68 contacts the legs of the wearer while in use.

In a preferred embodiment, the flap portion 68 and the backsheet 62 are joined directly to the other at the diaper 10 periphery adjacent and outboard of the proximal edges 64 by attachment means 88 such as adhesive bonding or any other attachment means such as an adhesive or any other attachment means such as heat/-pressure sealing, ultrasonic bonding or any other methods as are known in the art. For example, a uniform continuous layer of adhesive, a patterned layer of adhesive, or an array of separate lines or spots of adhesive may be used. The attachment means 88 are preferably a hot melt adhesive, such as the type manufactured by Eastman Chemical Products Company of Kingsport, Tenn., and marketed under the tradename Eastobond A-3 or the type manufactured by Century Adhesives, Inc. of Columbus, Ohio, and marketed under the tradename Century 5227.

As shown in FIG. 2, the channel portion 70 of the barrier cuff 62 comprises the portion of the barrier cuff 62 intermediate the proximal edge 64 and the distal edge 66 and generally defines the receiving channel 96. As shown in FIGS. 1 and 2, the channel portion 70 of the barrier cuff 62, and more particularly the proximal edge 64, is disposed adjacent and preferably inboard of the gasket cuff 56. The channel portion 70 of the barrier cuff 62 is disposed adjacent to the gasket cuff 56 to provide a more effective dual barrier system against the flow of body exudates. The proximal edge 64 is inboard of the gasket cuff 56 and preferably disposed intermediate the flap elastic member 60 of the gasket cuff 56 and the longitudinal centerline A—A of the diaper 10. More preferably, the proximal edge 64 is disposed intermediate the innermost flap elastic member 60 and the longitudinal edge of the absorbent core 18 in at least the crotch region 46 of the diaper 10.

The proximal edge 64 and the distal edge 66 are disposed in spaced relation to each other and define the effective width of the channel portion 70 of each of the barrier cuffs 62. The proximal and distal edges 64 and 66, respectively, may be in a parallel, nonparallel, rectilinear or curvilinear relationship. In addition, each of the barrier cuffs 62 may have a variety of different cross-sectional areas including circular, square, rectangular or any other shape such as that shown in FIGS. 2 and 3. Preferably, the proximal edge 64 is spaced from the distal edge 66 in a parallel and rectilinear relationship to provide a channel portion 70 having a uniform effective width. Each channel portion 70 of the barrier cuff 62 forms a receiving channel 96 in board of such channel portion 70 and below the distal edge 66. The receiving channel 96 forms a barrier to the flow of exudates as they tend to move or float across the topsheet 12. Thus, the receiving channel 96 restrains and holds exudates within the diaper 10 until it is removed from the wearer.

The channel portion 70 of the barrier cuff 62 is contiguous the flap portion 68 and defined by the proximal edge 64 and the distal edge 66. The proximal edge 64 is preferably formed by joining a segment of the barrier cuff member to the backsheet 16 by a seal means 78, such as an adhesive bead. The topsheet 12 overlays a portion of the body facing surface of the absorbent core 18 and terminates inwardly of and preferably adjacent the proximal edge 64, where the topsheet 12 is preferably joined to the proximal edge 64 of the channel portion 70 of the barrier cuff 62 by the seal means 78 to provide a leakage resistant seal along the proximal edge 64. This arrangement forms a leakage resistant seal along the proximal edge 64, presenting a barrier to liquids which may wick through the topsheet 12 and helping to prevent such liquids from wicking underneath the barrier cuff 62 to the edges of the diaper 10.

The distal edge 66 of the channel portion 70 of the barrier cuff 62 is disposed inboard of the proximal edge 64 and is free and unsecured to underlying components of the diaper 10. The distal edge 66 is formed by folding the end of the barrier cuff member back upon itself and joining the folded end to another segment of the barrier cuff member by the distal attachment means 92, forming a tunnel therewithin. The distal attachment means 92 is preferably an adhesive bead, comprising hot melt adhesive of the types discussed above.

A spacing means 76 such as a spacing elastic member 77 is enclosed in the tunnel and is joined to the barrier cuff 62. The spacing elastic member 77 may be preferably directly joined to the barrier cuff 62 by utilizing the pressure sensitive adhesive properties of the spacing elastic member 77. Alternatively, as shown by the spacing elastic attachment means 94. The distal edge 66 is thus spaced from the topsheet 12 by the elastic gathering action of the spacing elastic member 77. A receiving channel 96 is thus formed by the proximal edge 64 and the distal edge 66. The receiving channel 96 is shown open and ready to restrain and hold body exudates in the diaper 10 until it is removed from the wearer.

The seal means 78 of the present invention for joining the proximal edges 64 to the gasketing flaps 58 are shown in FIGS. 1, 2, and 3. The seal means 78 provide a leakage-resistant seal along the proximal edge 64 to present a barrier to the wicking of liquids through the topsheet 12 so as to prevent liquids from wicking underneath the barrier.cuffs 62 to the edges of the diaper 10.

In a preferred embodiment, as shown in FIGS. 1 and 2, the seal means 78 are positioned along the proximal edges, thus preferably inboard of the flap elastic members 60 in at least the crotch region 46 so that the topsheet 12 and preferably the absorbent core 18 do not extend beyond the seals means 78 in at least the crotch region 46 such that liquids may not wick past the seal means 78. While the topsheet 12 or the absorbent core 18 may extend beyond the seal means 78, protection against leakage of liquids emanating from the edges of the absorbent core 18 or wicking along the topsheet 12 is further provided by the leakage resistant seal formed by the attachment means 88 which joins the liquid impervious backsheet 16 to the liquid impermeable flap portion 68 of the barrier cuffs 62. The seal means 78 may be any means for securing the proximal edges 64 to the gasketing flaps 58 such as heat/pressure sealing, ultrasonic bonding, or any other methods as are known in the art. The seal means 78 are preferably an adhesive bead consisting of hot melt adhesives such as the adhesives manufactured by Eastman Chemical Products Company of Kingsport, Tenn., and marketed under the tradename Eastobond A-3 and by Century Adhesives, Inc. of Columbus, Ohio, and marketed under the tradename Century 5227.

The spacing means 76 for spacing the distal edge 66 from the topsheet 12 is any member which gathers, contracts, stiffens, shortens or otherwise acts on and is operatively associated with barrier cuff 62 so as to cause the it to stand up to provide a receiving channel 96 along the barrier cuff 62. The spacing means 76 preferably comprises one or more spacing elastic members 77. If so, the barrier cuffs 62 should be contractible so that the distal edges 66 may be sufficiently spaced from the topsheet 12 so that the receiving channel 96 is open to retain and hold body exudates within the diaper 10.

As shown in FIG. 1, the spacing elastic member 77 of the spacing means 76 is preferably operatively associated with each of the barrier cuffs 62 and disposed adjacent the distal edge 66. The spacing elastic member 77 is preferably joined to the barrier cuff 62 in an elastically contractible condition so that in a normally unrestrained configuration, the spacing elastic member 77 effectively contracts or gathers the distal edge 66 of the barrier cuff 62. The spacing elastic member 77 can be joined to the barrier cuff 62 in an elastically contractible condition in at least two ways as is discussed in the above referenced and incorporated U.S. Pat. No. 3,860,003 issued to Buell.

As shown in FIG. 2, the spacing elastic member 77 is operatively associated with the barrier cuff 62 by joining the spacing elastic member 77 within the barrier cuff 62 with a spacing elastic attachment 94 or directly to the barrier cuff 62 by the pressure sensitive adhesive properties of the spacing elastic member 77. The spacing elastic attachment 94 should be flexible and of sufficient adhesion to hold the spacing elastic member 77 in a stretched condition. The spacing elastic members 77 may be joined to the barrier cuff 62 adjacent only the ends of the spacing elastic member 77 if spacing elastic attachment is utilized. However, it is preferable to Join the entire length of the spacing elastic member 77 to the barrier cuff 62, and particularly preferable to utilize the pressure sensitive adhesive properties of the spacing elastic member 77 to do so. The spacing elastic members 77 may be ultrasonically bonded or heat/pressure sealed to the barrier cuff 62 using a variety of patterns. The spacing elastic attachment 94 is preferably glue beads made of hot melt adhesive such as marketed by Findley Adhesives of Wauwatosa, Wis. and marketed under the tradename Findley 581. If the spacing elastic member 77 is directly joined to the barrier cuff 62, it is not necessary that the barrier cuff 62 circumscribe such spacing elastic member 77. The pressure sensitive adhesive properties of the exposed face of the spacing elastic member 77 may be deactivated as described below. In this manner the tunnel of the barrier cuff 62 is obviated.

It will be apparent to one skilled in the art that one or more spacing elastic members 77 may be used to elasticize each barrier cuff 62. It will further be apparent to one skilled in the art that the spacing elastic members 77 may take a multitude of configurations. For example, the width of the spacing elastic members 77 may be varied; the spacing elastic members may comprise a single strand or several parallel or nonparallel strands of elastic material; or the spacing elastic members 77 may be rectilinear or curvilinear.

The spacing means 76 for spacing the distal edge 66 from the topsheet 12 may further comprise several other elements. For example, the barrier cuff 62 may have stiffening means disposed in or on each barrier cuff 62. The stiffening means must be sufficiently stiff so that the distal edge 66 is spaced away from the topsheet 12. Suitable materials for the stiffening means include foams, non-woven fabrics, batting, polyethylene film, formed films, spray glues, foamed elastomerics, polyester, polyurethane, or a high loft material as is manufactured by Carolina Formed Fabrics.

The spacing means 76 may also comprise means for shortening the length of the distal edge 66 in comparison to the length of the edges of the diaper 10. The distal edge 66 can be shortened by making a fold or pleat in the distal edge 66. This fold or pleat is secured by any of the holding means well known to those of ordinary skill in the art, such as adhesives or heat sealing. Alternatively, a section may be cut out of the distal edge and the resultant edges brought together to form a butt or lap joint. The distal edge 66 may also be shortened by attaching a length of the distal edge 66 to the topsheet 12 at a position other than where the distal edge 66 would lie when the diaper 10 is in a flattened out condition. Other shortening techniques as are known in the art may also be used.

The diaper may also comprise a closing means 80 for closing the ends 72 of the barrier cuff 62, as shown in FIGS. 1 and 3. The closing means 80 provide a more comfortable fit for the wearer and obviate inversion of the distal edge 66 of the barrier cuff 62 during application and use. As used herein, the term "inversion" is generally defined as the condition of the inboard disposed distal edge 66 turning outwardly when the diaper 10 is applied to the wearer. In a preferred embodiment as shown in FIGS. 1 and 3, such closing means 80 are disposed in the first and second waist regions 22 and 24 of the diaper 10. The remaining portions of the barrier cuff 62 are not closed, so that the distal edges 66 are freely openable. In a preferred embodiment, the closing means 80 are positioned in the entire front waist region 22, while the closing means 80 are positioned in only a portion of the back waist region 24. This construction is preferred so as to create the receiving channel 96 around the buttocks of the wearer.

As shown in FIG. 3, the distal edge 66 is joined to the underlying structure of the diaper 10, such as to the topsheet 12, inboard of the proximal edge 64 by a closing means 80 such as an adhesive bead. In this arrangement, the distal edge 66 is joined to and not intended to be spaced from the topsheet 12, so that inversion of the barrier cuff 62 is prevented. Preferably a spacing means 76, such as spacing elastic member 77 is not disposed in this region of the distal edge 66 because the distal edge 66 is preferably secured closed and is not designed to be spaced from the topsheet 12 in the waist regions 42 and 44. It should be recognized that while the receiving channel 96 is not open to restrain the flow of body exudates in the waist regions 42 and 44, the receiving channel 96 may still act to contain and hold exudates which migrate in a generally longitudinal direction.

While the closing means 80 may comprise any of several means as are known in the art such as ultrasonic bonding or heat/pressure sealing using a variety of bonding patterns or simple glues, the closing means 80 are preferably adhesive beads consisting of hot melt adhesives such as manufactured by Eastman Chemical Products Company of Kingsport, Tennessee, and marketed under the tradename Eastobond A-3 or Century Adhesives, Inc. of Columbus, Ohio, and marketed under the tradename Century 5227.

When the diaper 10 is applied to a wearer, in a known fashion, the containment function described hereinabove may occur. While worn, the distal edges 66 of the barrier cuffs 62 preferably extend to the groin area and diverge upwardly along the buttocks of the wearer. Either of the barrier leg cuffs encircle the thighs of the wearer. However, the gasket cuffs 56 do encircle the thighs of the wearer and create gasketing action thereagainst. The ends of the barrier cuff 62 are joined to the topsheet 12 to obviate inversion of the cuffs and provide for wearer comfort.

It will be apparent to one skilled in the art that variants of the numbers of elastic members 60 and 77 disclosed in the FIGURES may be employed. For example, either leg cuff 56 or 62 may have one or a plurality of elastic members 60 and 77. The elastic members 60 and 77 may be of the same or different geometries.

The barrier cuffs 62 may alternatively be joined to the backsheet 16, the topsheet 12, the absorbent core 18, or any combination of these and other elements of the diaper 10. In the preferred embodiment, the barrier cuffs 62 are integral with the gasketing flaps 58. The integral barrier cuffs 62 are thus preferably formed from a single strip of material with an intermediate segment joined to the gasketing flap 58 by the seal means 78, such as adhesives, to form the proximal edge 64, the distal edge 66. The distal edge 66 is formed by folding an end of the material back upon itself and being secured to another segment by the distal attachment means 92. The remaining portion of the material, specifically the flap portion 70, extends from and terminates outboard of the proximal edge 64, and is preferably associated with the backsheet 16 by attachment means 88 to define the gasketing flaps 58.

An alternative embodiment of the present invention provides that the topsheet 12 may extend outwardly beyond the proximal edge 64 of the barrier cuff 62 while still providing protection against liquids wicking out of the edges of the diaper 10. The barrier cuff 62 has a flap portion 68 that is affixed to the backsheet 16 to form the gasketing flap 58 by the attachment means 88 adjacent the edge of the diaper 10 so as to provide a leakage-resistant seal along the edge of the diaper 10. The flap portion 68 is preferably liquid-impermeable so as to provide the most effective leakage-resistant seal. The topsheet 12 may thus extend outwardly toward the edge of the diaper 10, beyond even the proximal edge 64 and/or the seal means 78, and need only terminate inwardly of the edge (i.e., the seal formed along the edge of the attachment means 88) of the diaper 10, liquids being thereby prevented from leaking or wicking from the edge of the diaper 10 due to the seal formed along the edge because the topsheet 12 is encased between the liquid impermeable flap portion 68 and the liquid impervious backsheet 16, and because the topsheet 12 terminates inwardly of the edge of the diaper 10.

In accordance with one aspect of the present invention, the leg cuffs 56 and 62 are elastically extensible in at least one direction, which direction is preferably generally longitudinal. As used herein, the term "elastically extensible" means able to be stretched, without rupture, from the free length at least about 50 percent, preferably at least about 100 percent, more preferably at least about 350 percent, held for about 15 seconds, and within about 5 minutes return to within about 10 percent of the free length upon release of the force which causes such elongation to occur.

Preferably, the leg cuffs 56 and 62 of the present invention are elastically extensible to about 50 percent to about 350 percent elongation without rupture and more preferably about 75 to about 150 percent elongation without rupture. As used herein, the term "rupture" means unintended separation of any constituent elements, tearing, fracturing, or breaking into two or more subparts. This property provides for conforming the disposable article 10 to the shape of the wearer's body and maintaining close contact of the leg cuffs 56 and 62 against the skin of the wearer. Leg cuffs 56 and 62 which are extensible, without rupture, to relatively greater elongations help to shape the diaper 10 into a generally concave upwards configuration which enhances the fit of the diaper 10 to the body of the wearer. Leg cuffs 56 and 62 which are elastically extensible to at least about 200 percent elongation without rupture are generally suitable to provide concave shaping of the diaper 10. Also, leg cuffs 56 and 62 which are relatively highly extensible can comfortably fit a larger range of sizes of wearers.

To prevent excessive forces from occurring when the leg cuffs 56 or 62 are stretched about the body of the wearer, the leg cuffs 56 and 62, through the respective elastic members 60 and 77, have an ultimate contact force of less than about 270 grams per centimeter (1.5 pounds per inch) width of elastic 60 or 77 upon elongation of the leg cuffs 56 or 62 between about 50 and about 350 percent and more preferably less than about 130 grams per centimeter (0.75 pounds per inch) of width upon elongation between about 50 and about 350 percent. Also the leg cuffs 56 and 62 have an incremental differential force per 50 percent elongation less than about 14 grams per centimeter of width. As used herein, the phrase "ultimate contact force" refers to the highest reading obtained on a tensile machine when a one centimeter wide sample of the elastic members 60 or 77 is pulled throughout the specified range of elongation, as described below. As used herein, the term "elongation" refers to change in length from the free length. For example, a sample which is extended to 100 percent elongation is twice the free length of the original sample.

More preferably, the elastic members 60 or 77 have an ultimate contact force of less than about 270 grams per centimeter width of elastic 60 or 77 when the leg cuffs 56 or 62 are elongated between about 75 to about 150 percent. More preferably, the elastic 60 or 77 has an ultimate contact force less than about 130 grams per centimeter (0.75 pounds per inch) of width when the leg cuffs 56 or 62 are elongated about 50 to about 350 percent and even more preferably, an ultimate contact force of less than about 130 grams per centimeter (0.75 pounds per inch) of width when the leg cuffs 56 or 62 are elongated about 75 to about 150 percent. As used herein the phrase "grams per centimeter of width" refers to the ratio of the highest reading from the tensile machine, in grams, when the sample is tested as described below to the cumulative width of the elastic members 60 or 77 in the sample. The gage length is taken parallel to the principal axis of elongation, if the sample is orthotropic or anisotropic. The width of the elastic members 60 or 77 is measured with the leg cuff 56 or 62 in an unstretched condition.

The ultimate contact force may be measured using a Instron Model 1122 tensile machine made by the Instron Corporation of Canton, Mass. utilizing a constant rate of elongation cross head traveling at a separation speed of about 50.8 centimeters per minute (20 inches per minute). A sample is taken lengthwise from the leg cuff 56 or 62. If the elastic members 60 or 77 have a cumulative width greater than 1 centimeter, a sample of any convenient gage length having a 1 centimeter cumulative width of the elastic members 60 or 77, taken perpendicular the principal axis of elongation of the leg cuffs 56 or 62, is selected. As used herein the phrase "cumulative width" refers to the sum of the widths of all elastic members 60 or 77 in the leg cuffs 56 or 62. If the cumulative width of the elastic members 60 or 77 is less than 1 centimeter, the sample of the leg cuff 56 or 62 is normalized to a 1 centimeter cumulative elastic member 60 or 77 width value.

The sample should then be extended, in tension, to and throughout the elongation range under consideration and the highest reading recorded. The ultimate contact force is then found according to the following formula: CP=T/W wherein CP is the ultimate contact force for the elongation range under consideration, T is the highest recorded tensile reading in grams, and W is the cumulative elastic member 60 or 76 width.

The differential force per 50 percent increment of elongation may be determined as follows. The sample of the leg cuff 56 or 62 is loaded into a tensile machine, as described above. The sample is elongated, in tension, until the gage length is increased approximately 50 percent and the resultant reading in grams, from the tensile machine, is recorded and divided by the original, unstretched, cumulative width of the elastic members 60 and 77. This calculation yields a first force measured in grams per centimeter. The sample is then further elongated, in tension, until an elongation of 100 percent from the free length is obtained. Again the resultant reading in grams, from the tensile machine, is recorded and divided by the original, unstretched, cumulative width of the elastic members 60 and 77. This calculation yields a second force n grams per centimeter. The first force is subtracted from the second force, yielding a "differential force" per 50 percent increment of elongation having units of grams per centimeter. This procedure is repeated, in 50 percent increments, until the free length of any lamina 13a, 13b, or 13c of the laminate or 350 percent elongation is reached.

All tensile readings should preferably be taken within about 5 seconds of reaching the desired elongation. A strip chart recorder may advantageously be utilized to obtain the readings which occur when the sample reaches the desired elongation.

A leg cuff 56 or 62 according to the present invention will preferably have a differential force per 50 percent elongation of less than about 14 grams per centimeter of initial width of the elastic members 60 and 77 and more preferably less than about 9 grams per centimeter of initial width of the elastic members 60 and 77.

One manner in which the desired force per incremental elongation properties, noted above, can be maintained is by providing leg cuffs 56 and 62 having elastic members 60 and 77 of relatively low contact force differential. A preferred embodiment of the elastic members 60 and 77 has a contact force differential less than about 7,030 kilograms per square meter (10 pounds per square inch), and a particularly preferred leg embodiment of the cuffs 56 and 62 has a contact force differential less than about 3,520 kilograms per square meter (5 pounds per square inch). As used herein, the term "contact force differential" is defined by the formula: $E=(F/A)/(\Delta L/L_0)$, wherein E is similar to the Young's modulus of elasticity in tension, but is not taken from the origin of the stress strain curve, F is the applied elongation force in kilograms, A is the cross sectional area of the sample prior to elongation in square meters, $\Delta L$ is the change in elongation from the free length in meters or any other convenient units, and $L_0$ is the length of the sample at 50 percent elongation measured in meters or any other convenient units of length, coincident with the units utilized to measure the change in elongation from the free length. The area A is the product of the sample width and thickness, or may be found by back calculating from the mass and density of the sample if the surface is irregular or the thickness is otherwise difficult to measure. The initial length and change in length are easily found using known techniques and instrumentation. The contact force differential may be thought of as the slope of the stress-strain curve taken within the range of elongation under consideration.

Alternatively, the aforementioned ultimate contact force within the desired range of elongations may be obtained through stress relaxation of the elastic members 60 and 77. As used herein, the term "stress relaxation" refers to the dissipation and diminution of stresses and the associated contractive and restoring forces which occur over time when a sample is elongated from its free length. Stress relaxation may be enhanced by application of heat or may occur due to elongation of the elastic members 60 and 77 to a range which causes slip of the molecular structure to occur. It is desired that the stress relaxation occurs after a relatively short period of time from the initial elongation of the leg cuffs 56 and 62 - so that the wearer does not experience discomfort caused by high contractive forces of the elastic members 60 and 77 for an undue length of time. Leg cuffs 56 and 62 having elastic members 60 and 77 which exhibit a stress of less than about 270 grams per centimeter (1.5 pounds per inch) of width, when tested as described above, after a period of at least at least about 10 minutes at a temperature of at least about 22° C. when elongated to a range of about 50 to about 350 percent are suitable. Generally, as the temperature of the elastic members 60 and 77 increases, greater stress relaxation occurs. The ultimate contact force is preferably less than about 270 grams per centimeter of width throughout the entire range of elongation, more preferably less than about 130 grams per centimeter (0.75 pounds per inch) of width throughout this range, and more preferably less than about 130 grams per centimeter of width under an elongation of about 75 to about 150 percent.

Referring to FIG. 4, if the generally preferred direct joining of the elastic members 60 and 77 to the leg cuffs 56 and 62 is not utilized, one embodiment of the elastic members 60 and 77 of the leg cuffs 56 and 62 which is suitable for use with the present invention is a laminate 13 having three laminae, two outboard laminae 13a and 13b, and an intermediate central lamina 13c. The central lamina 13c is elastically extensible, and is joined in face-to-face relation with the relatively inextensible outboard lamina 13a and 13b which face outwardly and define two opposed faces of the laminate 13.

The central lamina 13c is preferably elastomeric and more preferably an elastomeric adhesive. A pressure sensitive elastomeric adhesive is particularly preferred for the central lamina 13c, so that it may be readily joined to the outboard laminae 13a and 13b to form a unitary laminate 13. The adhesive selected for the central lamina 13c should also be capable of elongation from about 50 to about 800 percent in one or two principal directions without rupture, more preferably to at least about 1,000 percent without rupture, not exhibit excessive necking or thinning when elongated, or exhibit excessive hysteresis or delamination upon cycling. Within the desired range of elongations, the contact force differential of the central lamina 13c generally controls the contact force differential of the laminate 13, due to the outboard laminae 13a and 13b are generally relatively inextensible.

The outboard laminae 13a and 13b may be any flexible nonwoven fabric, apertured formed film, or any material commonly used in the art for leg cuffs 56 and 62. A preferred outboard laminae 13a and 13b material is a polyolefinic nonwoven fabric having a basis weight of about 4.2 to about 25 grams per square meter (5 to 30 grams per square yard). A particularly preferred outboard laminae 13a and 13b material is made of polyproylene and manufactured by the James River Corporation of Richmond, Va. and sold under the tradename Celestra.

The central lamina 13c of the laminate 13 is prestretched prior to joining of the central lamina 13c with the outboard laminae 13a and 13b. As noted above, after prestretching the central lamina 13c, the pressure sensitive adhesive property of the central lamina 13c provides for continuous face-to-face joining of the central lamina 13c with the outboard laminae 13a and 13b. Upon release of the force which causes prestretching of the central lamina 13c, the resulting laminate 13 gathers or contracts in the direction of prestretching. The resulting laminate 13 will be elastically extensible to the limit of prestretching of the central lamina 13c. If the laminate 13 is elongated beyond the amount of prestretch of the central lamina 13c, the free length of the relatively inextensible outboard laminae 13a and 13b will be exceeded. If this should occur, the ultimate contact force will sharply increase without significant further elongation and rupture will likely occur. Therefore, the central lamina 13c should be prestretched at to at least the desired limit of elongation, as noted above, to obviate high ultimate contact forces and rupture of the laminate 13. After rupture, the elastic properties of the central lamina 13c would control further elongation.

If the central lamina 13c is prestretched in two principal directions, the resulting laminate 13 will contract in both such directions, proportional to the magnitude of prestretching in each principal direction. However, a laminate 13 which is only longitudinally extensible has been found to work well for leg cuffs 56 and 62. The resulting laminate 13 is elastically extensible without rupture until at least the fully extended lengths of the outboard laminae 13a and 13b are reached.

If the central lamina 13c comprises a hot melt adhesive, the hot melt adhesive of the central lamina 13c should have a viscosity of about 9,000 to about 45,000 centipoises at a temperature of about 176° C. as measured according to ASTM Standard D3236-73. Pressure sensitive elastomeric adhesive marketed by the Findley Adhesives Corporation of Wauwatosa, Wisconsin under the tradename 198-338 has been found to be particularly well suited for this purpose.

It will be apparent to one skilled in the art that as the thickness and stiffness of the material to which the elastic members 60 and 77 are joined increases, the maximum elongation without rupture to which the laminate 13 may be extended will decrease. For relatively greater elongations, particularly elongations exceeding about 250 percent, a material such as the aforementioned nonwoven Celestra fabric is a suitable material.

Figure 5:
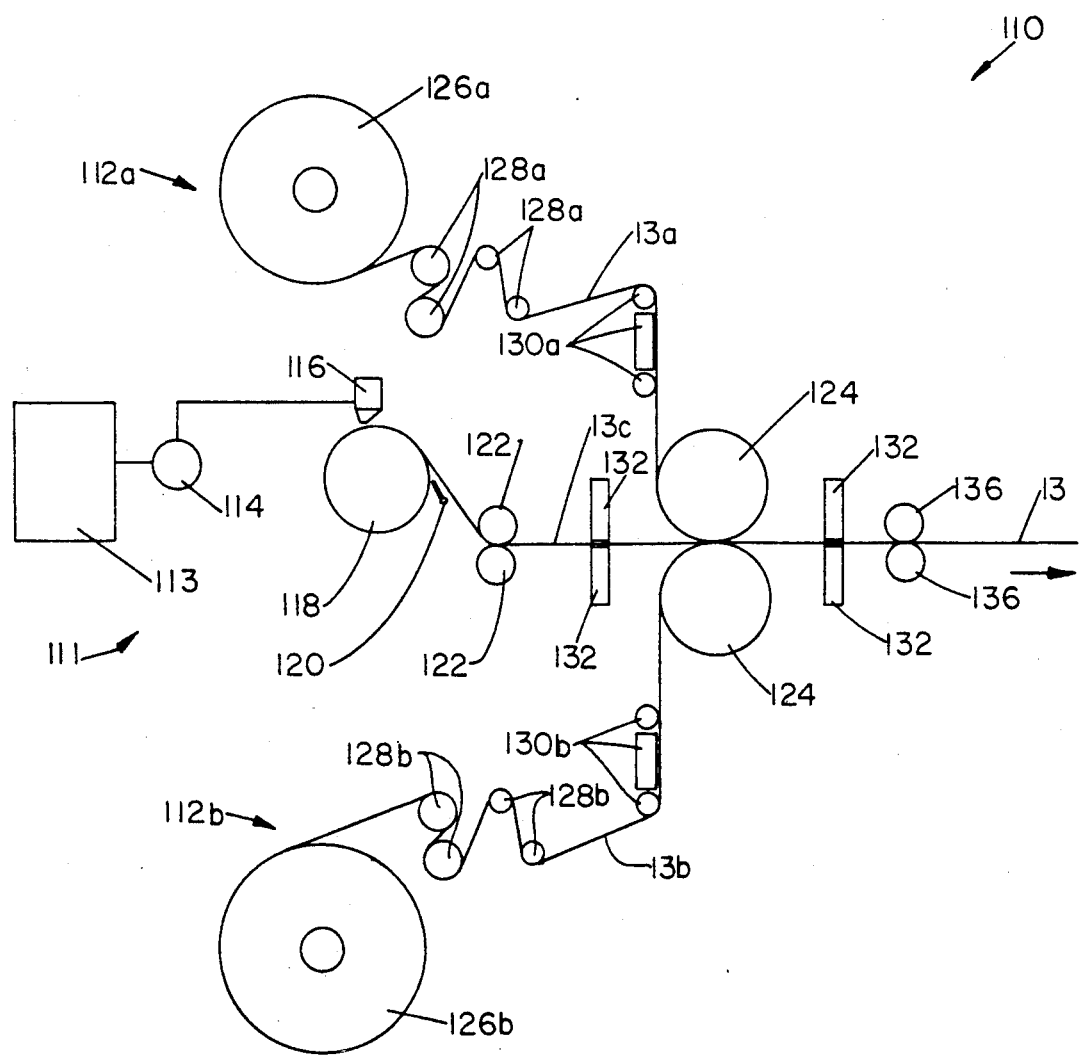
FIG. 5 is a side elevational schematic view of one apparatus which may be used to manufacture the elastic members of the leg cuffs of the present invention.

Referring to FIG. 5, the laminate 13 of the leg cuffs 56 and 62 of the present invention may be produced on the illustrated apparatus 110. The apparatus 110 comprises three separate lines, line 111 for the central lamina 13c, and complementary lines 112a and 112b for the outboard laminae 13a and 13b respectively.

The first line 111, utilized for the central lamina 13c, comprises an adhesive tank 113 used for storage of the hot melt adhesive supply, a pump 114 to transport the adhesive, an extrusion head 116 which extrudes the adhesive into a thin film and a chill roll 118 to form the web of the central lamina 13c. The outboard laminae 13a and 13b are formed on lines 112a and 112b. The materials used for the outboard laminae 13a and 13b are taken from unwind rolls 126a and 126b, passed through tensioning rolls 128a and 128b and, if desired, through tracking systems 130a and 130b. The combining rolls 124 join the confluent laminae 13a, 13b and 13c into a unitary laminate 13.

Examining FIG. 5 in more detail, the apparatus 110 comprises the means for joining at least two laminae in face-to-face relation. The central lamina 13c is formed from a supply of hot melt adhesive contained in the adhesive tank 113. The adhesive tank 113 is heated to maintain the hot melt adhesive of the central lamina 13c at a temperature of about 170 to about 180° C. The adhesive tank 113 is connected to a pump 114 designed to extract adhesive from the heated adhesive tank 113 without imparting excessive shear to the adhesive. A metering gear pump 114 has been found to be suitable for this purpose. Preferably, the adhesive is not recirculated while in the adhesive tank 113, or otherwise, to prevent excessive shear from being applied to the material of the central lamina 13c. Excessive shear may cause molecular breakdown of the material, resulting in a material of lower contact force.

The metering gear pump 114 supplies the adhesive, under pressure, to the extrusion head 116. The extrusion head 116 has a slot through which the molten elastic adhesive of the central lamina 13c is extruded to form a thin film of about 0.03 to about 1.0 millimeters (0.001-0.04 inches) in thickness, and of any desired width, onto the chill roll 118. A central lamina 13c of about 8.4 grams per square centimeter is suitable. A central lamina having a thickness of about 0.13 to about 0.38 millimeters (0.005 to 0.015 inches) is particularly preferred. Generally a thicker central lamina 13c is preferred as the thickness and stiffness of either outboard lamina 13a or 13b increases. It will be apparent to one skilled in the art that increasing the thickness of the elastomeric central lamina 13c will provide a proportional increase in the ultimate contact force of the laminate 13 of the leg cuffs 56 and 62.

The chill roll 118 cools the extruded adhesive of the central lamina 13c into a web of the laminate 13 suitable for further processing. The web of the central lamina 13c is separated from the chill roll by a doctor blade 120. If desired, a second roll (not shown) may be utilized in conjunction with the chill roll 118 to provide additional cooling and a nip for compression of the web of the central lamina 13c.

The central lamina 13c is then drawn through a nip formed between tensioning rolls 122. The tensioning rolls 122 provide for proper takeoff speed of the central lamina 13c from the chill roll 118 and further provide for proper entry of the central lamina 13c into the combining rolls 124.

The outboard laminae 13a and 13b are taken from the unwind rolls 126a and 126b and preferably pass through S-wrap tensioning rolls 128a and 128b to provide for proper tensioning and prevent puckering or bunching of the outboard laminae 13a and 13b. If necessary, a tracking system 130a and 130b, as is commonly utilized and known in the art, may be employed in either or both lines 112a and 112b to optimally track and adjust the web of outboard laminae 13a and 13b into the combining rolls 124. A tracking system manufactured by the Fife Corporation of Oklahoma City, Okla. and sold as Model No. Op6 LRA has been found to work well.

The laminae 13a and 13b enter the combining rolls 124 and pass through the nip formed therebetween. The nip of the combining rolls 124 compresses the laminae 13a and 13b into contacting relationship with the opposed faces of the central lamina 13c, causing the pressure sensitive adhesive of the central lamina 13c to bond to the outboard laminae 13a and 13b—joining the three laminae 13a, 13b and 13c.

The surface speed of the combining rolls 124 is greater than the surface speed of the adhesive tensioning rolls 122. This causes prestretching of the central lamina 13c in the machine direction, which prestretching is proportional to the differential surface velocity between the combining rolls 124 and the adhesive tensioning rolls 122, and the distance therebetween. As used herein, the term "machine direction" refers to the direction generally parallel to the travel of the laminate 13 as it passes through the nip of the combining rolls 124.

If desired, the laminate 13 need not incorporate two outboard laminae 13a and 13b. If desired, either or both outboard laminae 13a and 13b may be omitted from the laminate 13. Such a structure may be manufactured by providing selectively not operating the line 112a or 112b of the outboard lamina 13a or 13b desired to be omitted. The resulting laminate 13 has one lamina 13c, or two laminae 13a and 13c, with the central lamina 13c being of pressure sensitive elastomeric adhesive and the outboard lamina 13a being of relatively inextensible substrate materials.

After a two laminae laminate 13 exits the nip of the combining rolls 124, the exposed face of the central lamina 13c may be deactivated, by blocking as is commonly known in the art, so that the adhesive of the central lamina 13c does not bond to other materials through the pressure sensitive properties of the adhesive of the central lamina 13c. Blocking is accomplished by an adhesive deactivation system 132 applying a powder of resin to the exposed face of the central lamina 13c. Suitable resin powders include talcum powder, polyolefinic powders, and preferably a resin similar to that used for the outboard laminae 13a and 13b. If desired, the adhesive deactivation system 132 may be applied to the exposed face of the central lamina 13c prior to the central lamina 13c entering the nip of the combining rolls 124. Also, the laminate 13 may be heat sealed as desired.

If desired, one or both of outboard laminae 13a and 13b may be elastically extensible. The outboard laminae 13a and 13b may be of similar or different materials, as desired. It will be apparent to one skilled in the art that an adhesive deactivation system 132, should not be employed prior to the combining rolls 124 if a laminate 13 having two outboard laminae 13a and 13b is to be constructed using to the apparatus 110 of FIG. 5.

It will be apparent to one skilled in the art that several other variations in the invention disclosed herein are feasible without departure from the spirit and scope of the invention. For example, the leg cuffs 56 and 62 may have zones of differing elastic properties or may have inelastic zones. Inelastic zones may be created in the laminate 13 by a secondary heating process, such as heated rollers 136 that selectively provide localized heating to the zones of laminate 13 desired to be rendered inelastic.

Alternatively, a film of nonuniform thickness may be utilized for the outboard laminae 13a and 13b. As the thickness of the film increases, a greater force will be required for the same amount of extension to occur. All such variations are within the spirit and scope of the present invention.

What is claimed is:

1. A disposable absorbent article having two transverse waist portions and two longitudinal marginal portions, said article comprising:
   a liquid impervious backsheet;
   a liquid pervious topsheet at least partially peripherally joined to said backsheet;
   an absorbent core intermediate said topsheet and said backsheet; and
   at least one leg cuff disposed in each longitudinal marginal portion, each said leg cuff having at least one elastic member defining a cumulative width, wherein said leg cuff is elastically extensible in at least one direction and said leg cuff requires a force less than about 270 grams per centimeter of said cumulative width to elongate said leg cuff throughout the range of from about 75 percent to about 150 percent, and said leg cuff has a differential force per 50 percent increment of elongation less than about 14 grams per centimeter of said cumulative width.

2. A disposable absorbent article according to claim 1, wherein said leg cuff requires a force less than about 270 grams per centimeter of said accumulative width to elongate said leg cuff throughout the range of from about 50 percent to about 350 percent.

3. A disposable absorbent article according to claim 1 or 2 wherein said elastic member comprises a laminate having at least two laminae, wherein one lamina is elastically extensible and one lamina is relatively inelastic.

4. A disposable absorbent article according to claim 3, wherein said elastically extensible lamina is an elastomeric adhesive film.

5. A disposable absorbent article having two transverse waist portions and two longitudinal marginal portions, said article comprising:
   a liquid impervious backsheet;
   a liquid pervious topsheet at least partially peripherally joined to said backsheet;
   an absorbent core intermediate said topsheet and said backsheet; and
   at least one leg cuff disposed in each longitudinal marginal portion, each said leg cuff having at least one elastic member defining a cumulative width, wherein said leg cuff is elastically extensible in at least one direction and said leg cuff requires a force less than about 130 grams per centimeter of said cumulative width to elongate said leg cuff throughout the range of from about 75 percent to about 150 percent, and said leg cuff has a differential force per 50 percent increment of elongation less than about 14 grams per centimeter of said cumulative width.

6. A disposable absorbent article according to claim 5, wherein said leg cuffs have a differential force per 50 percent increment of elongation less than about 9 grams per centimeter of said cumulative width.

7. A disposable absorbent article according to claim 6, wherein said elastic member comprises a laminate having three laminae, comprising a central lamina, a first outboard lamina and a second outboard lamina, wherein said central lamina is elastically extensible and said first outboard lamina and said second outboard lamina are relatively inelastic.

8. A disposable absorbent article according to claim 7, wherein said elastically extensible central laminae is an elastomeric adhesive film.

9. A disposable absorbent article according to claim 8, wherein said elastomeric adhesive film is a hot melt adhesive and said first outboard lamina and said second outboard lamina are a polyolefinic nonwoven fabric.

10. A disposable absorbent article according to claim 5 or 8 wherein said at least one leg cuff is selected from the group consisting of a barrier leg cuff, a gasket leg cuff, or both a barrier leg cuff and a gasketing leg cuff.

11. A disposable absorbent article according to claim 5, wherein said leg cuff requires a force less than about 130 grams per centimeter of said cumulative width to elongate said leg cuff throughout the range of from about 50 to about 350 percent.

12. A disposable absorbent article according to claim 11, wherein said leg cuff has a differential force per 50 percent increment of elongation less than about 9 grams per centimeter of said cumulative width.

* * * * *